United States Patent
Ellman et al.

(10) Patent No.: US 6,395,001 B1
(45) Date of Patent: May 28, 2002

(54) ELECTROSURGICAL ELECTRODE FOR WEDGE RESECTION

(75) Inventors: Alan G. Ellman; Jon C. Garito, both of Hewlett, NY (US)

(73) Assignee: Health Care Technologies, LLC, Hewlett, NY (US)

( * ) Notice: Subject to any disclaimer, the term of this patent is extended or adjusted under 35 U.S.C. 154(b) by 0 days.

(21) Appl. No.: 09/546,697

(22) Filed: Apr. 10, 2000

(51) Int. Cl.[7] ............................................... A61B 18/18
(52) U.S. Cl. ......................................... 606/41; 606/45
(58) Field of Search ............................. 606/41, 45, 46, 606/47, 48, 49, 50, 34, 37, 39, 40, 110, 113, 162; 607/98, 145–147, 149

(56) References Cited

U.S. PATENT DOCUMENTS

| 5,078,716 A | * | 1/1992 | Doll ........................... 606/47 |
| 5,746,746 A | * | 5/1998 | Garito et al. .................. 606/32 |
| 5,897,554 A | * | 4/1999 | Chia et al. ..................... 606/41 |
| 6,117,109 A | * | 9/2000 | Eggers et al. ................ 604/114 |

\* cited by examiner

Primary Examiner—R. Kearney

(57) ABSTRACT

An electrode for use in an electrosurgical procedure for treating entropion by excising a wedge-shaped portion of the tarsus at the underside of a patient's eyelid. In a preferred embodiment, the electrode is uniquely configured to form a diamond-shaped support terminating in an active wire, generally V-shaped, whose width controls the width of the excised wedge, and the length of whose arms controls the thickness of the excised wedge. The active wire is supported by structure that is completely electrically-insulated to ensure excision only of the desired tissue while avoiding damage to surrounding tissue. The tissue incising is effected with the bare active wire at a depth stopped by a shoulder between the bare wire arms and the adjacent portions of the electrode support.

10 Claims, 2 Drawing Sheets

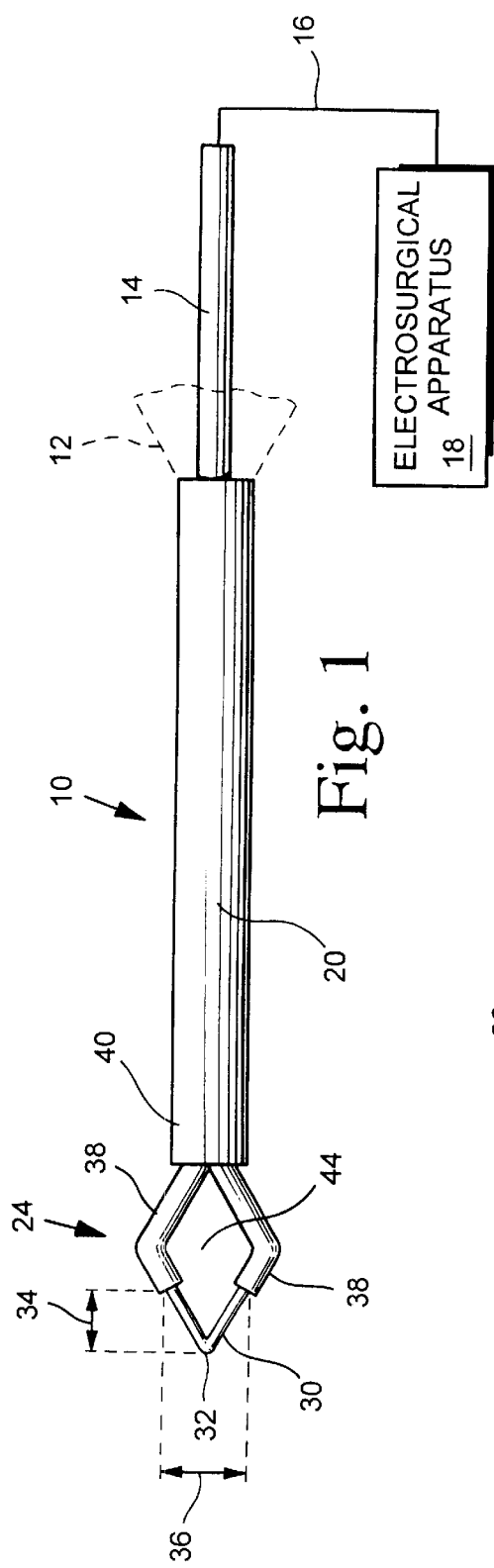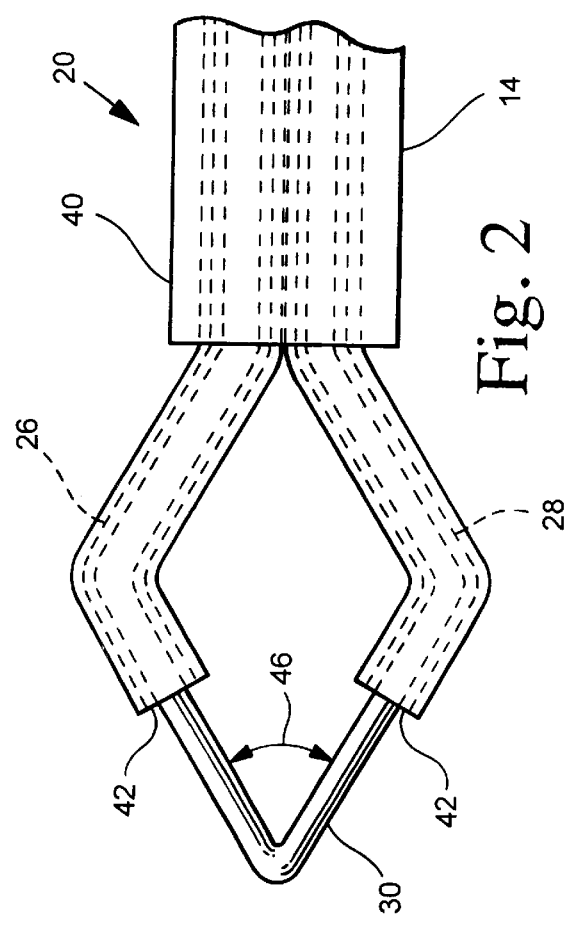

ELECTROSURGICAL ELECTRODE FOR WEDGE RESECTION

This invention relates to an electrosurgical instrument for wedge resection, and in particular, an electrosurgical electrode for use in treating entropion.

BACKGROUND OF THE INVENTION

Entropion is an inward rotation of the eyelid margin resulting in contact between the eyelashes and the cornea, which can cause inflammation and other disorders. A known procedure for treating this condition is to resect a tissue wedge from the underside of the upper eyelid using a traditional scalpel. Closing of the resultant incision tends to rotate the eyelid margin outwardly which sufficiently alters the shape of the eyelid margin as to effectively eliminate the problem.

The procedure is costly and difficult to control, especially the width and thickness of tissue removal, which ideally should be limited to the tarsal width and thickness, the tarsal being the dense connective tissue forming the support of the eyelid.

SUMMARY OF THE INVENTION

An object of the invention is an improved wedge resection surgical procedure using an electrosurgical instrument.

We have invented a novel electrode for use in an electrosurgical wedge resection procedure. This electrosurgical procedure using our novel electrode enables physicians to offer to patients a treatment that properly removes the correct amount of tarsal tissue, is easily learned and thus performed at a significantly reduced price, and with less tissue damage and bleeding compared to procedures done with a knife or blade.

The electrosurgical procedure using our novel electrode is based on performing essentially the same kind of wedge resection as was used heretofore but, in accordance with a feature of our invention, the structure of our novel electrosurgical electrode used to make the excision prevents the excision depth and width from exceeding a safe value.

In accordance with another feature of our invention, the electrode of the invention is uniquely configured to form an active thin wire, generally V-shaped, whose width controls the width of a V-shaped tissue groove, and the length of whose arms controls the thickness of the V-shaped tissue groove. The active wire is supported by structure that is completely electrically-insulated to ensure excision only of the desired tissue while avoiding damage to surrounding tissue, and to allow the physician to use these inactive insulated parts to help position and guide the active wire portion, which is the only part capable of incising tissue, and also serves as a stop during the surgical procedure. The electrosurgical procedure has the important advantage of being able to cut the tissue with minimum surgeon pressure while at the same time coagulating the cut tissue causing minimum bleeding. It is preferred that the electrosurgical currents used be above 2 MHz, and preferably above 3 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

BRIEF DESCRIPTION OF THE DRAWINGS

In the drawings:

FIG. 1 is a plan view of one form of electrosurgical instrument in accordance with the invention, shown connected to electrosurgical apparatus;

FIG. 2 is a partial plan view of the electrosurgical instrument of FIG. 1 showing interior structure.

DETAILED DESCRIPTION OF THE PREFERRED EMBODIMENTS

Figure 3:
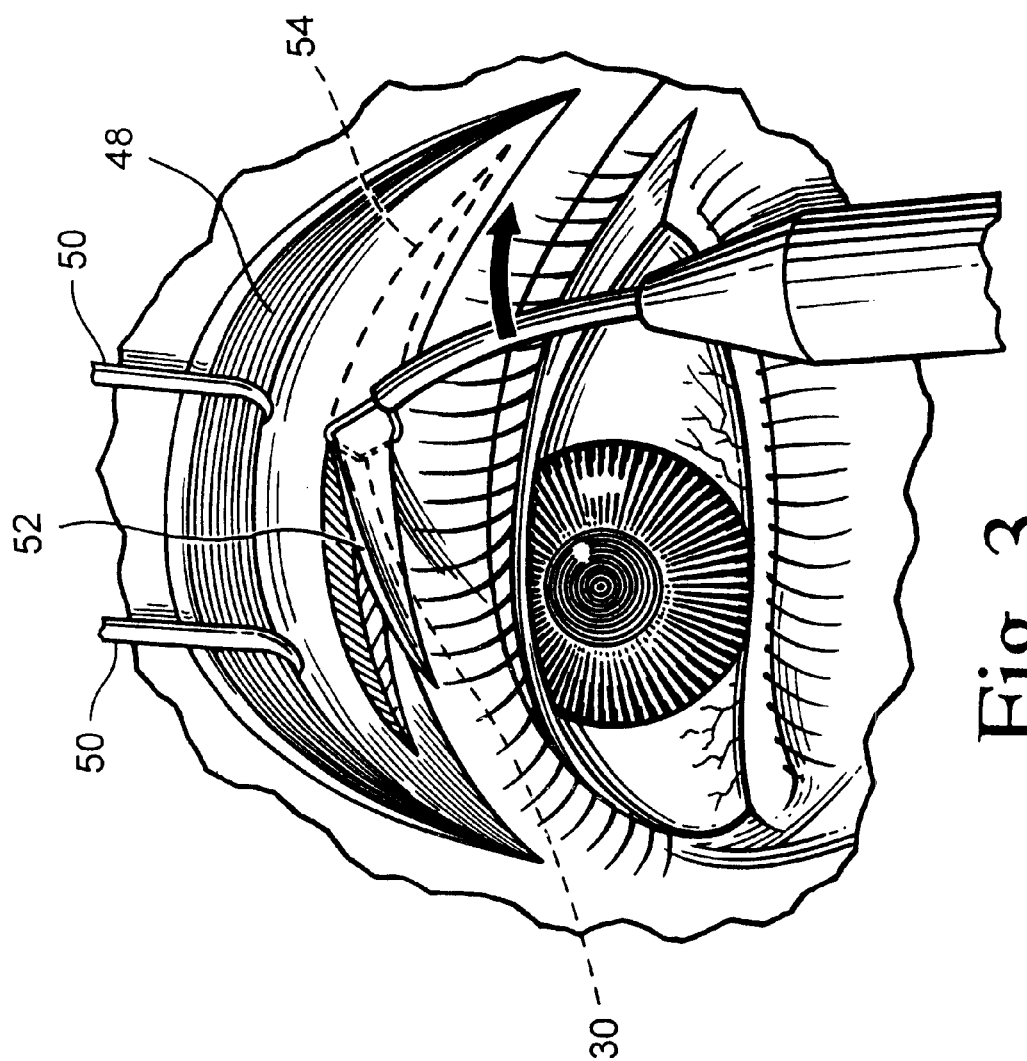
FIG. 3 is a schematic view illustrating the wedge resection procedure.

FIGS. 1 and 2 illustrate a preferred form of the novel electrosurgical instrument 10 of the invention. It comprises an elongated conventional handpiece 12 (only the collet end is shown in phantom) of electrically-insulating material having a central electrically-conductive brass tube or conductor 14 extending throughout its length and connected at its end to a cable 16 which is connected in the conventional manner to conventional electrosurgical apparatus 18. As an example only, the electrosurgical apparatus can be any radiosurgical instrument available from Elhman International, Inc. of Hewlett, N.Y. The Elhman equipment is preferred due to its high operating frequency, typically above 3 MHz, preferably from about 3.5–4 MHz. This particular apparatus provides electrosurgical currents at approximately 3.8 MHz.

At the opposite end of the handpiece 12 is mounted an electrosurgical electrode 20 which comprises the electrically-conductive straight axial brass rod 14 running lengthwise through it and mounted at its end nearest the handpiece 12 in the handpiece collet and thus electrically connected to the cable 16. The distal end of the electrode comprises an electrically-conductive, generally partial diamond-shaped support 24 comprising two stiff support arms 26, 28, such as metal bent tubes, for example of stainless steel, supporting a very fine metal wire, for example, of tungsten, 30. The metal wire 30 forms a closed V having a peak 32 at the distal end and its free ends encased in the support arms 26, 28 extend together with the latter into the interior of the brass tube 14 to which they are solidly anchored in a good electrically conductive manner. Also connected to the electrosurgical apparatus 18 is the usual indifferent plate (not shown) which during use is in contact with a patient's body. When the electrosurgical apparatus 18 is energized, high frequency electrosurgical currents are generated which are coupled by way of the cable 16, electrically-conductive tube 14, and electrically-conductive tubes 26, 28 to the active, bare V-shaped bare wire 30. The physician, in the usual way, holds the handpiece 12 while applying the active working end 30 of the electrode to the desired area of the patient to be treated.

In accordance with a feature of the invention, the active electrode portion 30 comprises a very fine, thin wire, for example, 0.004 inches in diameter of tungsten. FIG. 3 schematically shows a patient's eye with upper eyelid 48 retracted 50 upward exposing the tarsus on the lid underside. The wedge 52 excised has a triangular or V shape determined by the V-wire 30. The V-wire 30 when activated penetrates into the tarsal tissue to the full depth of the bare arms 30, indicated by the reference numeral 34. Due to the shape of the V, the width of the tarsal wedge excised is determined by the width of the V, indicated by the reference numeral 36. When activated, the active wire 30 cuts cleanly and easily with little pressure required through the tissue.

As will be observed, the portion of the diamond extending from the bare V 30, which includes the metal tubes 26, 28 is covered with a thin layer 38 of an electrically-insulating material, and the adjacent portion of the brass tube is also covered with a layer 40 of electrically-insulating material. The thinner active wire arms 30 form, where each meets the wider electrically-insulated support arms 26, 28, a shoulder 42 which acts as a stop when the active wire 32 is inserted into tissue during the procedure and thus controls the depth of the incision.

Electrically-insulated electrode sections which cannot contribute electrosurgical currents cannot cut tissue. With a size of the tungsten wire of, for example, 0.004 inches, and a typical diameter of the insulated support arms 26 of about 0.032 inches, a shoulder 42 is formed having a radius of about 0.016 inches, which is sufficient to prevent tissue penetration exceeding the axial length of the wire arms 30. That length is preferably set at about 1.0 mm or somewhat larger so that the tissue wedge thickness excised will have a slightly smaller value, say 0.8 mm. For this embodiment, the width is preferably set at about 3–4 mm. The area designated 44 inside of the diamond loop formed by the active wire portions 30 and the arms 26, 28 is deliberately left empty. When the active wire end 30 of the electrode is inserted into the tissue up to the stops 42, the cutting begins by pulling the electrode along the skin. The tissue wedge as it becomes excised passes upward through the clear loop area 44 and then is typically grasped with forceps and lifted clear so the surgeon can clearly see without any obstacles the cutting site from both sides and the manner in which the cutting is occurring to ensure a uniform excision.

The metal support arms 26, 28 function to support the fine tungsten wire in its V-shape.

In accordance with a further feature of the invention, the arms 26, 28 of the diamond support as well as the remaining part of the electrode shaft 20 up until it joins the bare end 14 is covered with the coatings 38, 40 of the electrically-insulating material. The coating 40 for the straight shaft part of the electrode may be one of many suitable electrically-insulating rubber or plastic materials. The coating 38 on the diamond support 24 comprises a thinner coating of an electrically-insulating material, which may be one of many suitable thin electrically-insulating plastics, baked Teflon being one example. Thus, the entire length of the electrode 20 from the bare active wire end 30 to the bare end 14 which is mounted in the handpiece 12 is electrically insulated from the patient. The handpiece 12, too, is completely electrically-insulated.

The V-shape of the active wire end 30 is critical to achieve the desired object, which is to allow the physician to apply the electrode portion 30 to the tarsal tissue, activate the apparatus, and with relative ease penetrate the region with the bare wire 30 up to the dual stops 42, and then move the instrument in the required path to make the desired wedge incision without fear of exceeding a safe depth of penetration, which preferably is up to about 90% of the tarsus thickness. The insulating coatings 38 and 40 are essential to prevent accidental burning or other tissue damage by the sides of the electrode as the instrument is manipulated over the skin of the patient.

As mentioned, preferably the transverse width 36 of the longitudinal active wire portion 30 is about 4 mm to obtain a 2–3 mm wide wedge. If desired, the width of the wire portions 30 can be increased to about 5 mm for a wider wedge, or reduced to about 1.5 mm for a narrower wedge. The slab thickness is determined by the axial length of the V-arms 30. Preferably, that length is about 1.0 mm but can vary from about 0.8–3.5 mm. Preferably the angle subtended by the V-arms, indicated by reference numeral 46 is about 60°, but can vary between about 50–70° The configuration of the active end lends itself to the manufacture of a family of electrodes capable of providing wedges of various thicknesses and widths. For example, the same configuration as illustrated in FIG. 1 but with active wire portions 30 of different widths, say from 1–3 mm, will provide a first family of electrodes capable of providing excised grafts of about the same thickness but with different widths. Similarly, a second family can be provided with different axial lengths 34 of about 0.6–3 mm.

With the Ellman equipment, the fully rectified or cut/coag current is used at a power setting of about 3–4 with the active bare wire electrode 30. There is very little trauma and the sore area felt by the patient at the eyelid site is easily handled by analgesia and anti-inflammatory and antibiotic drugs.

It will also be understood that the electrode of the invention is not limited to its use for a wedge resection procedure. To those skilled in this art, there will certainly be other uses for this novel electrode that provides a V-shaped active wire tip, with adjacent electrode sections coated with insulating material for accurately guiding and controlling the position of the active tip during a tissue incising electrosurgical procedure.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for performing a V-shaped wedge excision of tissue from the underside of a patient's eyelid for treating an entropion condition, comprising:

(a) an electrically-conductive shaft member having a longitudinal direction and a first end for mounting to a handpiece and a second end, (b) said second end comprising a fixed generally diamond-shaped support structure comprising first and second outwardly-extending electrically-conducting arm portions each connected to the second end of the electrically-conductive shaft member, the diamond-shaped support structure further comprising third and fourth inwardly-extending electrically-conducting arm portions each connected, respectively, to one of the first and second arm portions and joined together at their ends to form an electrically-conductive, wire portion having a V-shape and a V-apex of the diamond-shaped support structure where joined, (c) the outwardly-extending first and second arm portions and the adjacent parts of the inwardly-extending third and fourth arm portions being coated with an electrically-insulating coating leaving uncoated the parts remaining of the third and fourth arm portions up to where they join to form the V-apex which remains bare of the electrically-insulating coating, (d) said bare arm portions at the V-apex being exposed electrically for forming an active wire portion for applying electrosurgical currents to said eyelid tissue when said shaft member is connected to a source of electrosurgical currents, (e) the electrically-insulating coated portions of the diamond-shaped support structure and of the adjacent parts of said shaft member being electrically-insulating to prevent contact and passage of electrosurgical currents to areas adjacent to or surrounding the V-shaped wedge tissue to be excised, (f) the V-apex forming the active wire portion being dimensioned such that the V-shaped wedge tissue excised from the underside of the eyelid will when the incision is closed effectively treat the entropion condition.

2. An electrosurgical electrode as claimed in claim 1, wherein the bare arm portions of the third and fourth arm portions forming said active wire portion at their widest have a width not exceeding about 5 mm and with an axial length not exceeding about 3.5 mm.

3. An electrosurgical electrode as claimed in claim 2, wherein the coated arm portions of the third and fourth arm portions adjacent the bare active wire portion have a larger diameter than that of bare arm portions of the third and fourth arm portions forming with each of the latter a shoulder acting as a stop preventing tissue penetration of the active wire portion beyond the length of its bare arm portions.

4. An electrosurgical electrode as claimed in claim 3, wherein the peak of the V-shaped bare arm portions, at the V-apex have an axial length (34) between about 0.8 and 1 mm and a width (36) between about 1.5 and 5 mm.

5. An electrosurgical electrode as claimed in claim 4, wherein the bare arm portions of the active wire portion are each constituted of a thin wire having a diameter of about 0.004 inches.

6. An electrosurgical electrode as claimed in claim 5, wherein the first, second, third and fourth arm portions are each straight.

7. In combination:
  a handpiece having means at one end for connection to electrosurgical apparatus capable of supplying high frequency currents and having at its opposite end means for mounting an electrically-conductive shaft of an electrosurgical electrode and for supplying the high frequency currents to said electrode;
  an electrosurgical electrode for performing a V-shaped wedge excision in an eyelid surgical procedure as claimed in claim 6, mounted to the opposite end of the handpiece.

8. The combination of claim 7, wherein the high frequency currents are at a frequency exceeding 3 MHz.

9. A eyelid wedge excision surgical procedure for the treatment of entropion in a patient, comprising the steps:
  (a) providing electrosurgical apparatus connected to a handpiece holding a unipolar electrosurgical electrode for performing a V-shaped wedge excision of tissue, said electrosurgical electrode comprising:
    (i) an electrically-conductive shaft member having a longitudinal direction and a first end for mounting to a handpiece and a second end,
    (ii) said second end comprising a generally diamond-shaped support structure comprising first and second outwardly-extending electrically-conducting arm portions each connected to the second end of the electrically-conductive shaft member, the diamond-shaped support structure further comprising third and fourth inwardly-extending electrically-conducting arm portions each connected, respectively, to one of the first and second arm portions and joined together at their ends to form an electrically-conductive, wire portion having a V-shape and a V-apex of the diamond-shaped support structure where joined,
    (iii) the outwardly-extending first and second arm portions and the adjacent part of the inwardly-extending third and fourth arm portions being coated with an electrically-insulating coating leaving uncoated the remaining parts of the third and fourth arm portions up to where they join to form the V-apex bare of the electrically-insulating coating,
    (iv) said bare arm portions at the V-apex being exposed electrically for forming an active wire portion for applying electrosurgical currents to said tissue when said shaft member is connected to a source of electrosurgical currents,
    (v) the electrically-insulating coated portions of the diamond-shaped support structure and of the adjacent part of said shaft member being electrically-insulating to prevent contact and passage of electrosurgical currents to areas adjacent to or surrounding the V-shaped wedge tissue to be excised,
    (vi) means forming a shoulder where said active wire portion meets the adjacent portions of the inwardly-extending third and fourth arm portions, said shoulder being sufficiently wide to prevent tissue penetration of said active wire portion beyond its length,
    (vii) the V-apex forming the active wire portion being dimensioned such that when the V-shaped wedge tissue is excised from the underside of the eyelid and when the incision is closed the entropion condition will be effectively treated,
  (b) applying the active wire portion of the electrode to the tarsus tissue at the underside of the eyelid of a patient and activating the electrosurgical apparatus,
  (c) penetrating the tissue of the patient until stopped by the means forming a shoulder,
  (d) excising a wedge-shaped portion of the tarsus with the active wire portion of the electrode by moving the electrode through the tissue,
  (e) closing the incision to alter the shape of the eyelid margin to treat the entropion condition.

10. A eyelid edge excision surgical procedure for the treatment of entropion in a patient as claimed in claim 9, wherein the thickness of the wedge-shaped portion of the tarsus excised is about 1 mm.

* * * * *